US006428504B1

(12) United States Patent
Riaziat et al.

(10) Patent No.: US 6,428,504 B1
(45) Date of Patent: Aug. 6, 2002

(54) MULTIPURPOSE TEMPLATE AND NEEDLES FOR THE DELIVERY AND MONITORING OF MULTIPLE MINIMALLY INVASIVE THERAPIES

(75) Inventors: Majid L. Riaziat, San Jose; George A. Zdasiuk, Portola Valley; Robert M. Sutherland, Menlo Park; Andrew G. Jeung, Mountain View; Steven Bandy, Sunnyvale, all of CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 09/544,346

(22) Filed: Apr. 6, 2000

(51) Int. Cl.[7] ............................................. A61M 31/00
(52) U.S. Cl. ...................................................... 604/65
(58) Field of Search ........................... 604/65, 20, 21, 604/60, 68; 600/407

(56) References Cited

U.S. PATENT DOCUMENTS

| | | | | |
|---|---|---|---|---|
| 4,173,228 A | | 11/1979 | Van Steenwyk et al. .... 128/653 |
| 4,292,960 A | * | 10/1981 | Paglione ........................ 600/2 |
| 4,427,005 A | | 1/1984 | Tener ...................... 128/303 R |
| 4,733,661 A | | 3/1988 | Palestrant .................... 128/303 |
| 5,626,829 A | | 5/1997 | Koutrouvelis ............... 424/1.11 |
| 5,797,849 A | | 8/1998 | Vesely et al. ................ 600/461 |
| 5,868,757 A | | 2/1999 | Koutrouvelis ................ 606/130 |
| 6,142,991 A | * | 11/2000 | Schatzberger ................ 128/898 |
| 6,251,100 B1 | * | 6/2001 | Flock et al. ................... 604/20 |
| 6,251,102 B1 | * | 6/2001 | Gruzdev et al. .............. 372/34 |
| 6,315,772 B1 | * | 11/2001 | Marchitto et al. ............ 604/21 |
| 6,328,735 B1 | * | 12/2001 | Curley et al. ................. 606/14 |
| 6,330,479 B1 | * | 12/2001 | Stauffer ....................... 607/101 |

OTHER PUBLICATIONS

"Interstitial Electrodes Allowing Longitudinal Control of SAR Distributions", Stavros D. Prionas, Peter Fessenden, Daniel S. Kapp, Donald R. Goffinet, George M. Hahn, pp. 707–710 plus cover, Proceedings of the 5th International Symposium on Hyperthermic Oncology, Kyoto, Aug. 29–Sep. 3, 1988, Hyperthermic Oncology 1988, vol. 2, Special Plenary Lectures, Plenary Lectures and Symposium and Summary Workshops, Taylor & Francis, 1989.

* cited by examiner

*Primary Examiner*—Teresa Walberg
*Assistant Examiner*—Vinod D Patel
(74) *Attorney, Agent, or Firm*—Dorsey & Whitney LLP

(57) ABSTRACT

An apparatus and method to implement and control a plurality of minimally invasive therapies in the treatment of a medical condition of a patient based on a treatment plan. The apparatus includes a template which has a plurality of electrically conductive apertures, a plurality of needles which have a plurality of sensors and a processor. At least one of the needles is inserted through and in electrical contact with one of the conductive apertures. The processor is electrically coupled to the template and is configured to send signals to and receive signals from at least one of the sensors of at least one of the needles inserted through one of the conductive apertures. The processor is further configured to process the signals received from the sensor in relation to the treatment plan and to adjust the signals sent to the sensor to control the treatment.

47 Claims, 11 Drawing Sheets

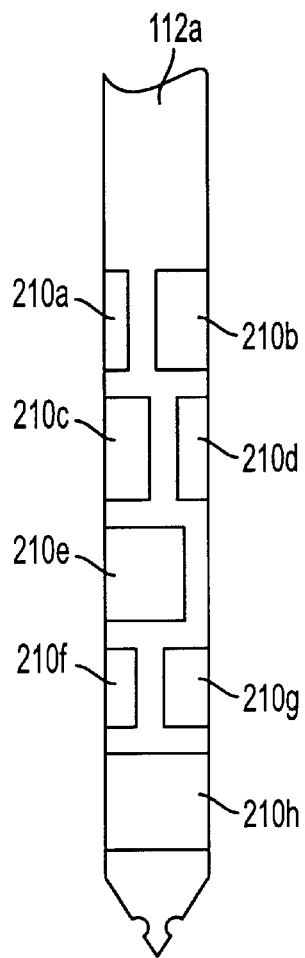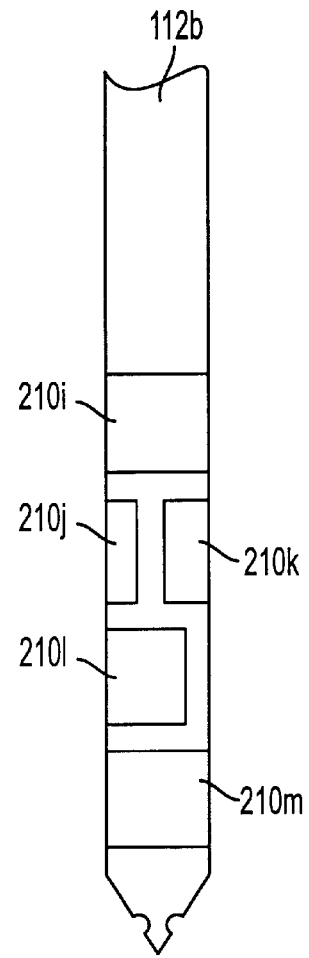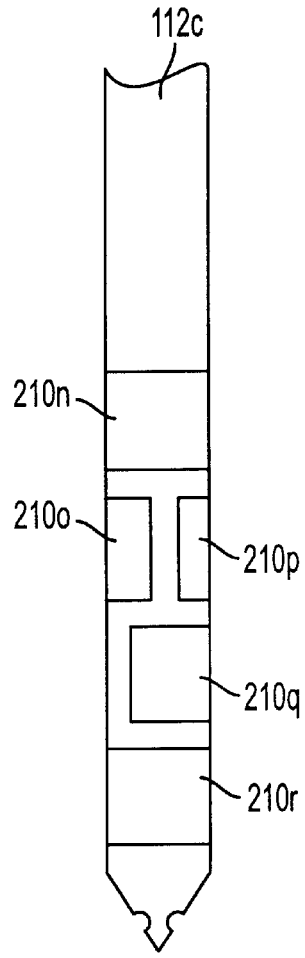
FIG. 7D-1  FIG. 7D-2  FIG. 7D-3

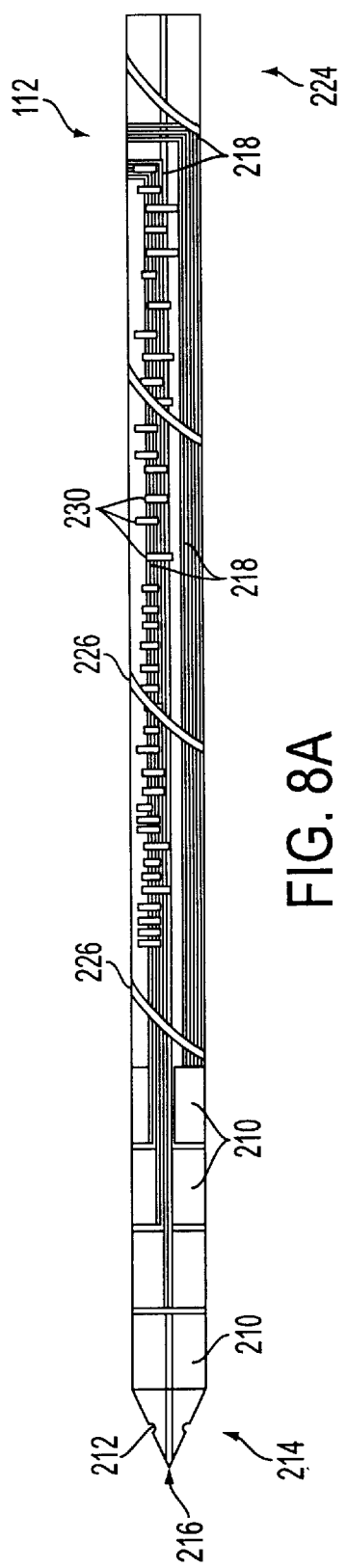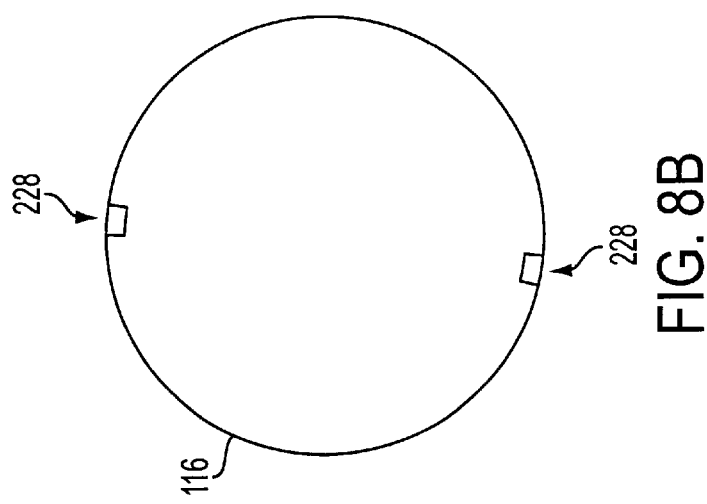

MULTIPURPOSE TEMPLATE AND NEEDLES FOR THE DELIVERY AND MONITORING OF MULTIPLE MINIMALLY INVASIVE THERAPIES

BRIEF DESCRIPTION OF THE INVENTION

The present invention relates to the treatment of ailments within the body of a patient, and more particularly, to an apparatus and method for focusing medical treatment of cancerous or tumorous tissue.

BACKGROUND OF THE INVENTION

It has long been desired to treat certain medical conditions, such as cancer, by focusing the treatment specifically to the affected area. By focusing the treatment, higher concentrations of treatment can be utilized without seriously damaging the surrounding, non-affected tissue.

Many techniques have been tried, including the insertion of a plurality needles directly into the affected tissue to perform specific therapeutic treatments, for example, gene therapy, brachytherapy and electroporation. One of the initial problems with directly inserting needles was the accuracy of placement of the needles. To increase accuracy, rigid templates with through holes have been used to guide the needles.

The techniques used to implement the therapeutic treatments vary widely. Microwave technologies utilizing a plurality of antennae placed into the affected tissue has been tried, but this technique is not easily automated. Hyperthermia has also been performed by heating the needle with an electrical heating element, hot water, ferromagnetic seeds and RF-driven electrodes. However, the prior art has had difficulty controlling the distribution of heat with these methods. The use of a localized sensor for heat generation solves some of these problems, however, the heat generators of the prior art only allow the control of heat in two dimensions utilizing a plurality of needles spaced a distance apart.

Needle placement techniques generally require methods of verifying final placement of the needles. X-ray has been used to help determine the accuracy of the final position. This technique is time consuming, costly and requires the patient to be exposed to potentially high amounts of radiation. Ultrasound has also been used to determine the final placement of needles. However, the reflected ultrasound waves are very often too weak to obtain an accurate reading. Further, the needles have small diameters, thus producing a very small amount of reflection.

One of the problems with the prior art approaches to therapies utilizing a plurality of placed needles within the affected tissue is that the control of the therapy requires direct wiring of the needles or fixed hard printed circuit board for a single application. Further, the prior art does not provide an effective way to both monitor and control the therapy. Nor does the prior art provide an effective way of implementing, controlling and varying the therapy in a three dimensional approach. Further, the prior art cannot implement multiple therapies utilizing a single needle positioned within a single template. The control of the prior art therapies are not highly automated, thus requiring a large amount of doctor and technician time to implement and complete.

OBJECTS AND SUMMARY OF THE INVENTION

It is a general object of the present invention to provide a method and apparatus for implementing, monitoring and adjusting the treatment of an affected area of a patient's body.

It is another object of the present invention to provide an automated system for implementing and controlling treatments of affected tissue.

It is a further object of the present invention to deliver and control the treatment in three dimensions.

It is still a further object of the present invention to provide for verification of the placement of the needles.

The foregoing and other objects of the invention are achieved by an apparatus and method to implement and control a plurality of minimally invasive therapies in the treatment of a medical condition of a patient. The treatment is based on a treatment plan. The apparatus includes a template which has a plurality of electrically conductive apertures, a plurality of needles which have a plurality of sensors and a processor which includes a memory block for storing the treatment plan. At least one of the needles is inserted through and in electrical contact with one of the conductive apertures. The processor is electrically coupled to the template and is configured to send power and signals to and receive signals from at least one of the sensors of at least one of the needles inserted through one of the conductive apertures of the template. The processor is further configured to process the signals received from the sensor in relation to the treatment plan and to adjust the signals sent to the sensor to control the treatment.

BRIEF DESCRIPTION OF THE DRAWINGS

The foregoing and other objects of the invention will be more clearly understood from the following description when read in conjunction with the accompanying drawings in which:

FIG. 7D shows an enlarged partial side view of a first end of three needles in simultaneous operation.

FIG. 8A shows a side view of needle including a spiral groove and optical pattern.

FIG. 8B shows a top view of an aperture of the rigid plate of the template including pins.

DESCRIPTION OF PREFERRED EMBODIMENTS

Figure 1:
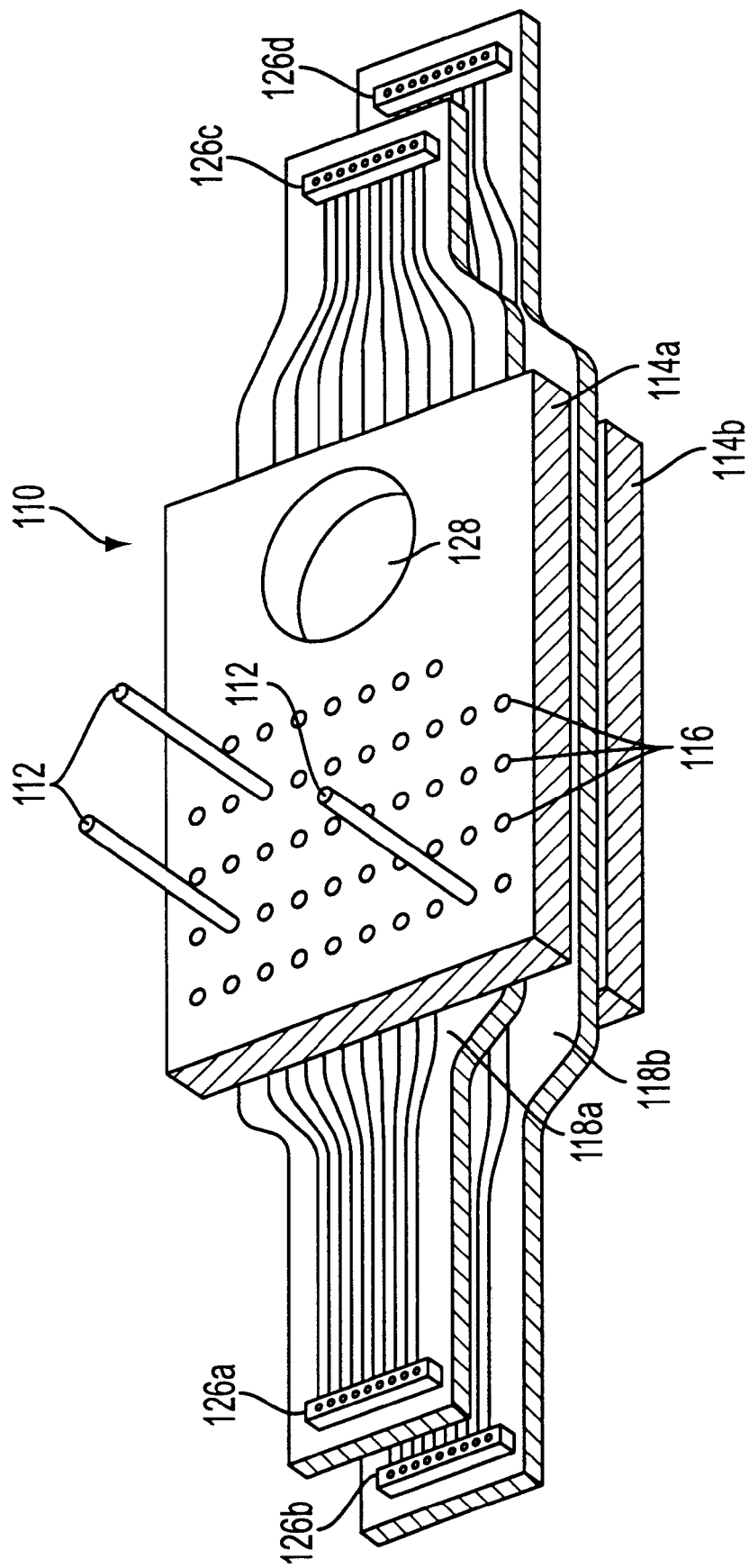
FIG. 1 shows a perspective view of a multipurpose template including two flexible PCBs and needles inserted through the template.

FIG. 1 depicts one embodiment of the present invention. The present invention provides for an apparatus and method of performing a variety of therapeutic treatments on affected tissue within the body of a patient. The therapies which can be implemented through the present apparatus and method include, but are not limited to, hyperthermia, brachytherapy, conformal chemotherapy, gene therapy, electroporation, etc. The therapeutic treatments are performed through the use of a plurality of multipurpose catheters or needles 112 which are guided into proper positioning within the tissue to be treated through a multipurpose template 110. The template 110 includes at least one substantially rigid plate 114 and at least one flexible printed circuit board (PCB) 118. FIG. 1 depicts an embodiment which includes two rigid plates 114a, 114b, and two flexible PCBs 118a, 118b. The needles 112 are guided into proper positioning within the tissue to be treated by inserting the needles 112 through one of the plurality of apertures 116 formed within the rigid plates 114 of the template 110. The rigid plates 114 provide stability and positioning for the needles 112. The needles 112 are electrically coupled to at least one flexible printed circuit board (PCB) 118 through electrically conductive apertures (shown in FIGS. 3A–B and 4) formed within the flexible PCB 118. The flexible PCB 118 couples to a processor 124 (see FIG. 10A) through connector ports 126a–d, thus providing electrical coupling between the needles and the processor 124. The processor 124 can be any signal generating or monitoring device as are known in the art such as a computer, a microprocessor, a pulse generator, a temperature monitor, or any combination of signal generators and monitors to implement and control the treatment.

Multipurpose template 110 is designed for the treatment of a plurality of therapies. Generally, a specific template is designed for use on a specific body part of a patient. For example, one template can be designed for prostate treatment, while another template can be designed for cranial treatment, and yet another template can be designed for abdominal treatment, etc. Depending on the requirements for the differing treatments, the templates can be configured differently.

Figure 2A:
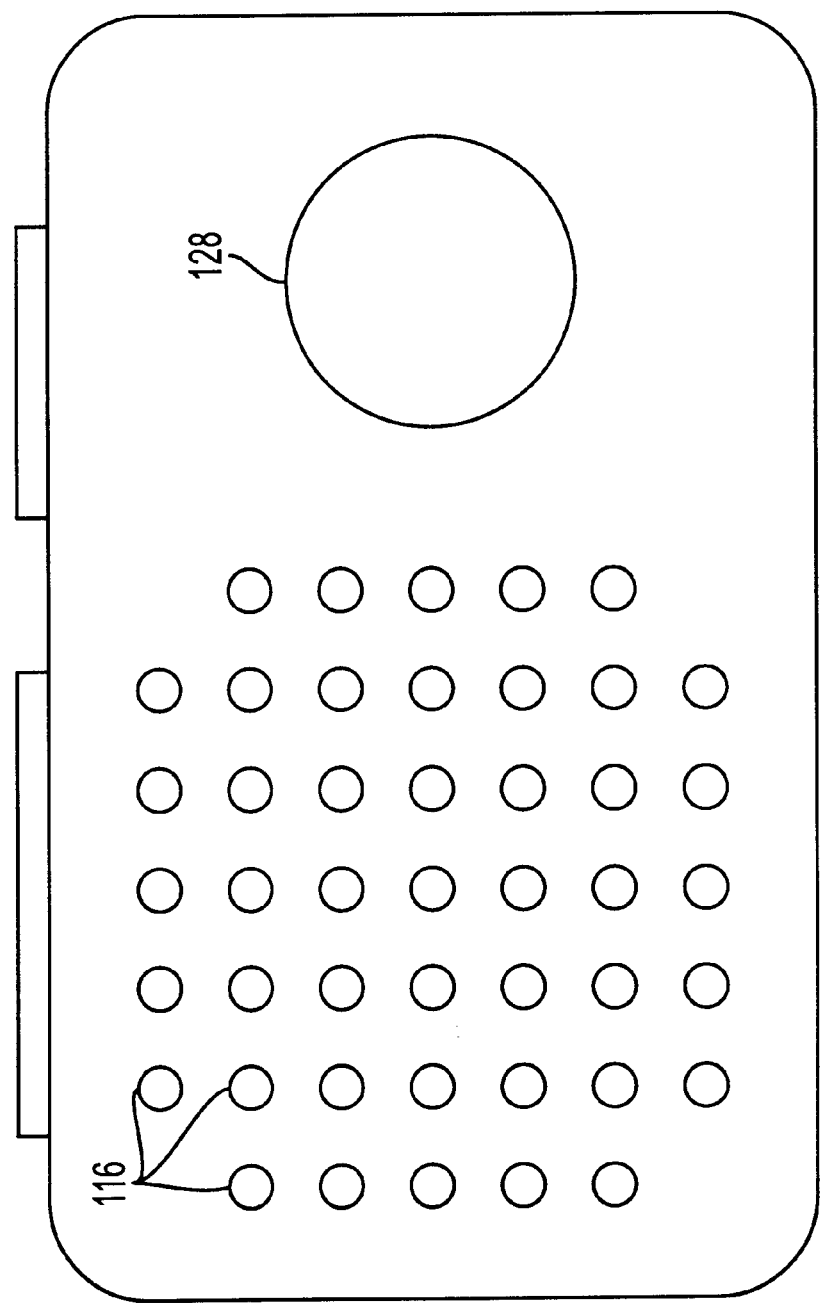
FIG. 2A shows a top view of a rigid plate including a plurality of apertures.

To further illustrate the components of the multipurpose template 110, FIG. 2A depicts one embodiment of the substantially rigid plate 114 of template 110. The rigid plate 114 is constructed of any electrically insulating, externally biocompatible material, such as Delrin™, plexiglass, or medical grade elastomer. Apertures 116 are arranged within rigid plate 114 to meet certain criteria for performing specific treatments, for example pancreatic cancer, prostate cancer and the such. A large aperture 128 can also be provided within rigid plate 114 to allow an ultrasound generator/receiver (not shown) to be positioned on the template 110 to monitor the insertion of the needles 112 into the tissue to be treated. The thickness 130 of the rigid plate 114 (depicted in FIG. 2B) is designed to provide sufficient stability to the template 110 and ensure proper alignment of the needles 112 into the affected tissue.

Figure 2B:
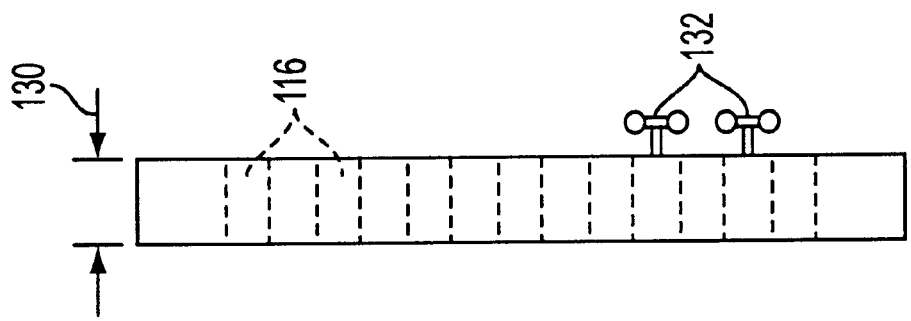
FIG. 2B shows a cross-sectional side view of the rigid plate of FIG. 2A.

FIG. 2B also depicts one embodiment of a micromotor 132 fixed to the rigid plate 132 of the template 110. The motor 132 can be coupled to a connector port 126 which connects to the processor 124. Needles 112 are inserted into the aperture and in movable connection with the micromotor 132. The motor engages the needle through a pair of rubber wheels that grab and drive the needle. Alternatively, motor 132 can engage needle 112 through a rotating collar around the needle 112 that drives the needle through a spiral groove on the needle 112; or needle 112 can include a column of teeth for engaging the motor which has a matching wheel for driving the needle. The processor 124 can control the direction of motor 132 to move the needle 112 into or out of the aperture 116 thus providing control of the depth of penetration of the needle 112 into the affected tissue. The depth of the penetration is measured roughly through the history of the steps taken by the motor. Alternatively, in one embodiment, precise measurement of needle insertion depth or positioning is done by monitoring an optical pattern on the needle. The optical pattern can be affixed on the needle through various well know techniques, for example, scribing or etching. In one embodiment the optical pattern is monitored through a light diffraction monitoring device which can direct light onto the optical pattern and receive diffracted, reflected light from the needle. Alternatively, the pattern can be viewed by technician or doctor implementing the treatment plan.

Figure 3A:
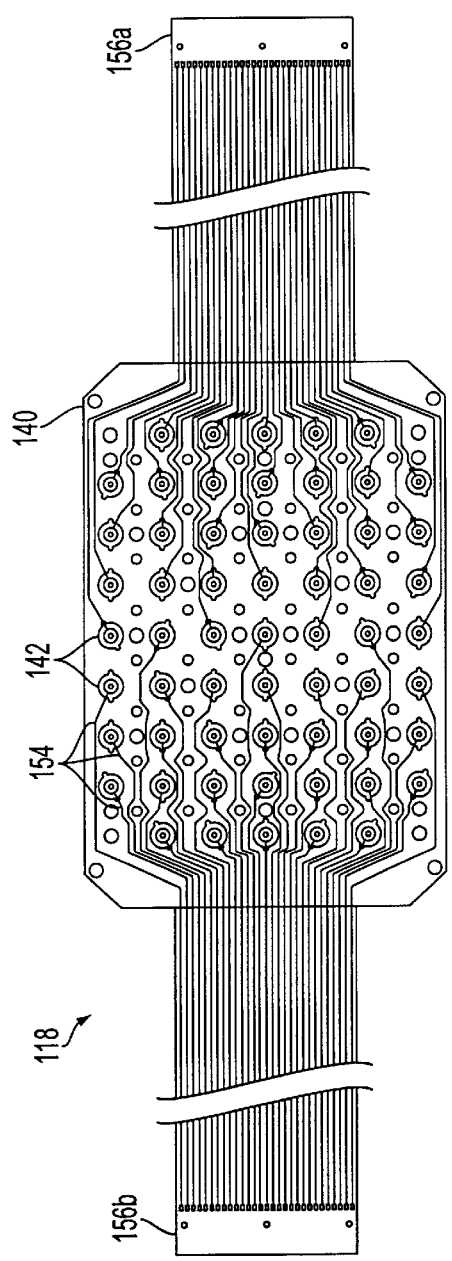
FIG. 3A shows a top view of one embodiment of a flexible PCB including conductive apertures, conductive leads and connector ports.
Figure 3B:
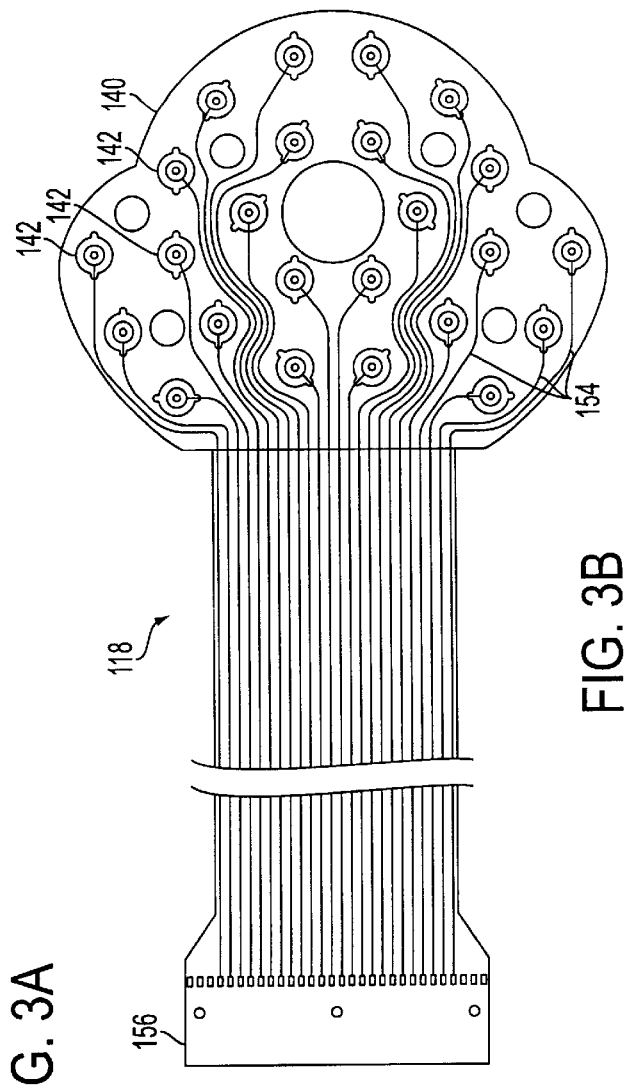
FIG. 3B shows a top view of an alternative embodiment of a flexible PCB including conductive apertures and conductive leads.
Figure 4:
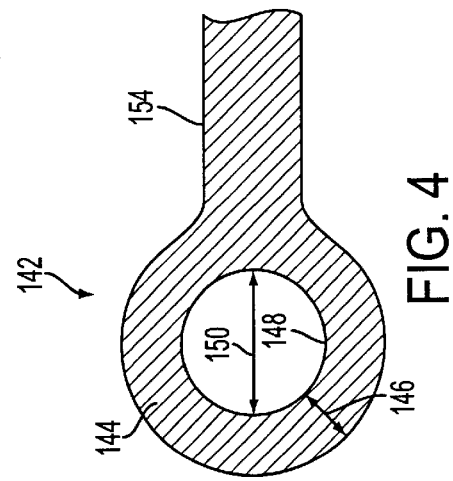
FIG. 4 shows a top view of a conductive aperture of a flexible PCB of FIG. 3A or 3B.

FIG. 3A shows one embodiment of the flexible PCB 118. The flexible PCB 118 is also designed for treatments on certain areas of the patient's body. FIG. 3B shows an alternative embodiment of the flexible PCB 118. Flexible PCB 118 is secured within template 110 by being sandwiched between rigid plates 114 or between insulating layers 186. The rigid plates 114 and insulating layers 186 are fastened together with screws, clamps or such, securing the template 110 and thus the PCBs 118. The structural body 140 of the PCB 118 is constructed of polyimide or polyester manufactured by DuPont™ or MicroSi™, which provides a sufficient degree of rigidity while still allowing the PCB 118 to be flexible. The flexible PCBs 118 are specifically designed for specific areas of a patients body to be treated, or for specific treatment plans. The flexible PCBs 118 are also designed to correspond to the rigid plates 114. The flexible PCB 118 includes a plurality of conductive apertures 142. The conductive apertures 142 are geographically laid out to corresponds with the rigid plate apertures 116. The conductive apertures 142 are constructed of a layer of conductive metal 144 which extends a predetermined distance 146 from the inner radius 148 of the aperture, as shown in FIG. 4. The diameter 150 of the conductive aperture is designed to be large enough to allow a needle 114 to pass through the aperture. In one embodiment the conductive metal 144 is copper with a tin or gold coating over the exposed surfaces. For a thermocouple connection, the conducive metal would be one used in a thermocouple junction; e.g., copper or constantan. The conductive aperture 142 is configured to electrically couple to a needle 112 which is inserted through the conductive aperture 142 and into a patient for treatment. Each conductive aperture 142 is electrically coupled to a conductive lead or ribbon cable 154 which is normally constructed of the same conductive metal 144 used to construct the conductive aperture 142.

Referring back to FIG. 3A, each conductive lead 154 extend from its respective conductive aperture 142 to one of two connector ports 156a, 156b. The conductive leads 154 are insulated from one another by the polyimide or polyester material of the structural body 140 of PCB 118. The embodiment of the PCB 118 shown in FIG. 3A is designed with two connector ports 156. A single-port design or a multi-port design can also be implemented. The connector ports 156a–b are design to couple to a processor line 312 (see FIG. 10) which is directly coupled to a processor or computer 124 (see FIG. 10) which can process information received from and direct control signals to the needles 112 inserted into and in electrical contact with the conductive apertures 142. Connector ports 156a–b can be common computer connector ports as are well known in the art, such as a D-subminiature connector or ZIF connector. In one embodiment of the flexible PCB 118, the connector ports 156 are AMPMODU™ connectors from AMP Incorporated of Harrisburg, Pa.

Referring back to FIG. 1, multiple flexible PCBs 118a, 118b can be combined into a single template 110. The PCBs 118a, 118b are separated by a non-electrically conductive insulating layer 186 (shown in FIG. 6). The insulating layer is constructed of any electrically insulating, externally biocompatible material. Examples include, but are not limited to, Delrin™, plexiglass, and medical grade elastomer. The insulating layer 186 provides electrical insulation between PCB's 118 as well as securing the electrical contact devices 170. This allows each PCB 118 within a template 110 to be utilized independently from one another. The processor can direct each PCB 118 to perform a specific function, such as electroporation or temperature sensing, independent of the other PCBs 118 within the template 110 which can be directed to perform other functions. Thus, each PCB 118 can perform a specific function apart from the other PCBs 118. This allows multiple therapies and monitoring to be performed simultaneously utilizing a single template 110 by directing specific needles to perform specific functions through the individual PCBs 118. Further, the multi-layered template 110 enhances the present inventions ability to perform treatments in a three dimensional approach by allowing separate PCBs 118 within the template 110 to activate independent sensors on individual needles 112.

The flexible PCBs 118 can be easily removed from the template 110 and replaced with a different PCB 118. This allows the multipurpose template 110 to be specifically configured for each patient or each procedure. Further, because the PCBs 118 are easily removed and are resistant to heat, they can be easily cleaned and sanitized for reuse on other patients. Thus, the template 110 of the present invention provides a great degree of flexibility in implementation.

Figure 5A:
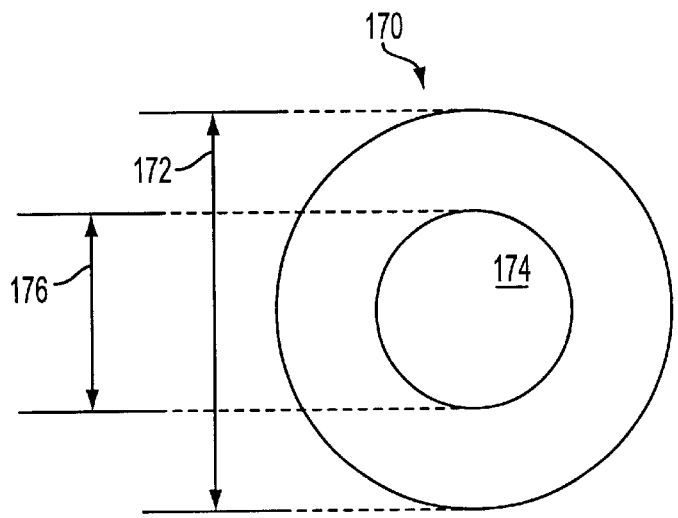
FIG. 5A shows a top view of an electrical contact device.
Figure 5B:
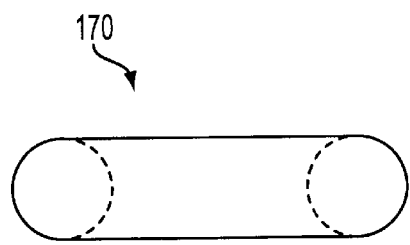
FIG. 5B shows a cross-sectional side view of the electrical contact device of FIG. 5A.
Figure 5C:
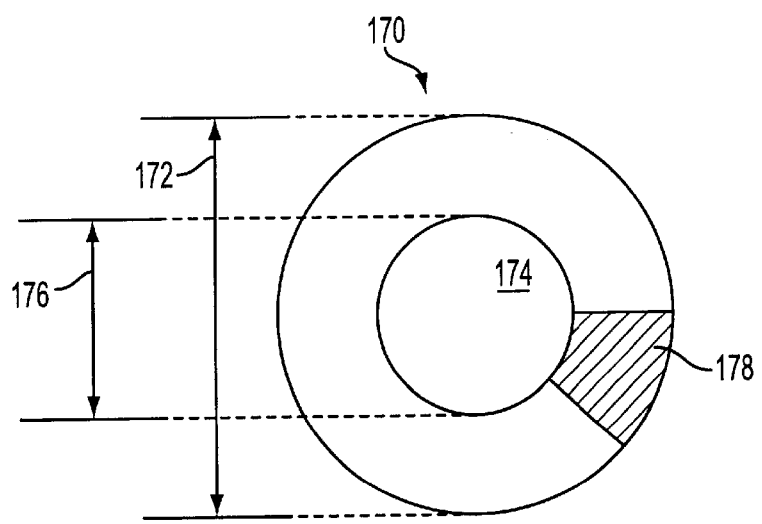
FIG. 5C shows a top view of the electrical contact device including a conductive section.

In one embodiment the needles 112 can be electrically coupled to the conductive apertures 142 of PCB 118 through an electrical contact device or electrical contact ring 170. FIGS. 5A & 5B depicts one embodiment of an electrical contact device 170. The electrical contact device 170 in this embodiment is formed from an electrically conductive, compressible foam. This electrically conductive foam consists of a non-conductive resilient polymer (such as silicone) infused with conductive fillers (such as nickel and/or carbon) to give a volume resistivity on the order of 10-3 to 10-4 ohm-cm. FIG. 5C depicts an alternative design for the electrical contact device 170 where the contact device 170 is only electrically conductive along a single conductive section 178. The conductive section 178 can be constructed through infusing the electrical contact device 170 with conductive filler or a section of elastic, conductive metal. Design parameters of the electrical contact device 170 include hardness, tensile strength, tear strength and compression/deflection under load. The material is cast in molds to specifications, and manufactured by Instrument Specialties located in Water Gap, Pa.

The electrical contact device 170 is designed to have an outer diameter or dimension 172 which is greater than the diameter 150 of the conductive aperture 142 of the PCB 118. This allows the electrical contact device 170 to be positioned on and in electrical contact with a conductive aperture 142. The electrical contact device 170 is held firmly against the conductive aperture 142 by the pressure exerted on it by either the rigid plate 114 or one of the insulating layers 186 (see FIG. 6). The inner aperture diameter 176 of the electrical contact device 170 is designed to be smaller than the diameter 150 of the conductive aperture 142. The inner aperture diameter 176 is also configured to be smaller than the cross-section of a needle 112. Thus, when a needle 112 is inserted into a conductive aperture 142, it must pass through the inner aperture 174 of the electrical contact device 170. Because the electrical contact device 170 is a compressible foam, when a needle is inserted into the inner aperture 174 of the electrical contact device, the electrical contact device 170 is compressed radially outward. This compression of the electrical contact device 170 provides the electrical contact between the needle 112 and the conductive aperture 142. The inner aperture diameter 176 is further configured to provide a compression force sufficient to resist the movement of the needle. This resisted movement secures the needle to a desired position and resists the movement of the needle from moving in and out of the conductive aperture 142 and thus maintains the position of the needle 112 within the tissue to be treated.

Alternative embodiments for the electrical contact device 170 can include collets, snaps, springs and other contact devices known in the art to provide electrical contact between the conductive aperture 142 and the needle 112.

Figure 6:
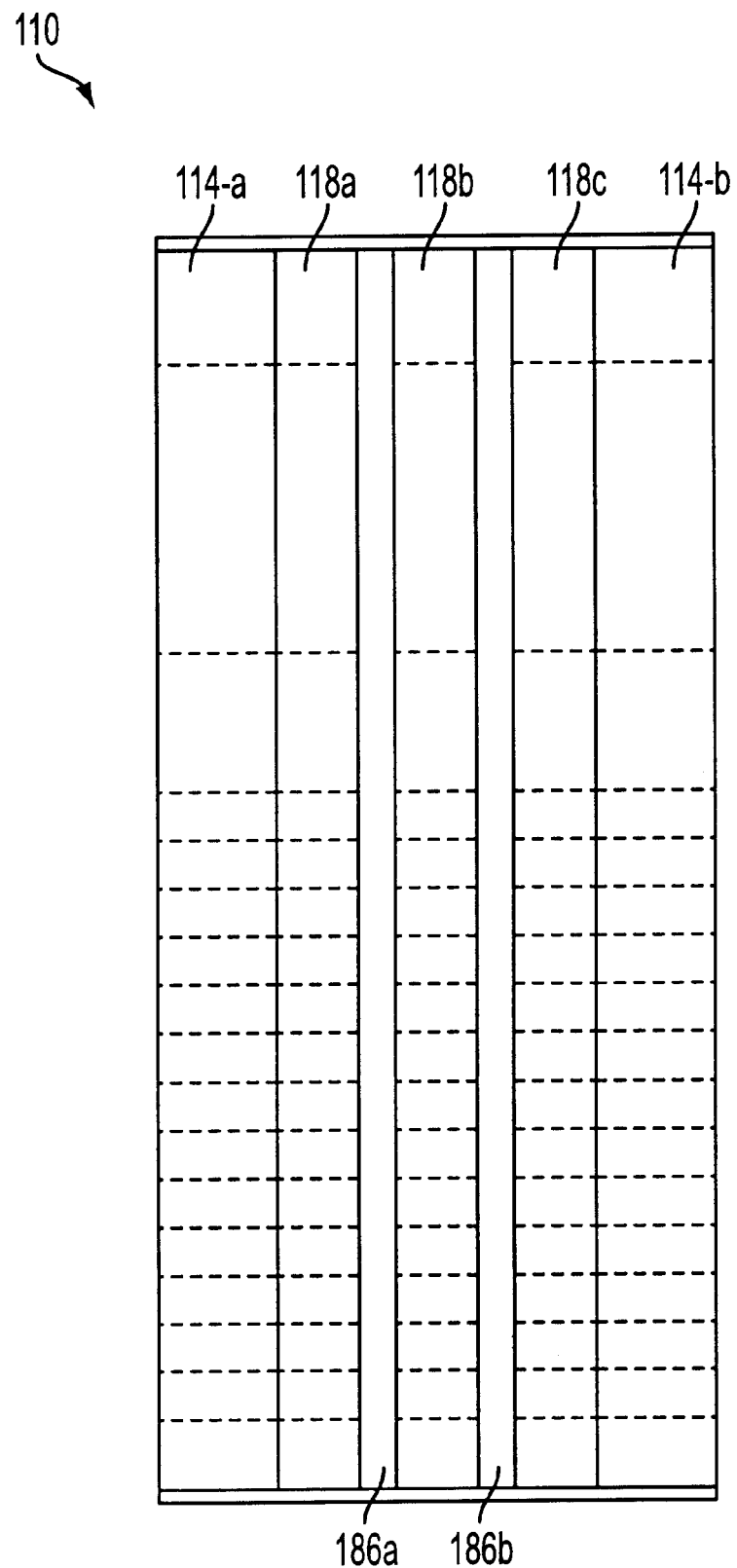
FIG. 6 shows a cross-sectional side view of the template including a plurality of rigid plates, flexible PCBs and insulator layers.

The template 110 is further designed to provide the ability to specifically configure the template through multiple layers. These layers can include rigid plates 114, flexible PCBs 118 and insulating layers 186. FIG. 6 shows a cross-sectional view of a template 110 which includes two rigid plates 114a–b, three flexible PCBs 118a–c, and two insulating layers 186a–b. The insulating layer 186 provide insulation between the flexible PCBs 118. Electrically separating the PCBs 118 allows a first PCB 118a to perform a first function or treatment while a second PCB 118b performs a second completely different function or treatment and a third PCB 118c performs a third different function or treatment. This can continue for N number of layered PCBs 118. Because each PCB 118 is coupled to a processor 124, each PCB can be directed to perform specific functions or treatments. For example, the first PCB 118a can perform heat generation, while the second PCB 118b performs temperature measuring, while the third PCB 118c performs electroporation. The treatments are performed through the needles 112 inserted and electrically coupled to the conductive apertures 142 through the electrical contact device 170.

Figure 7A:
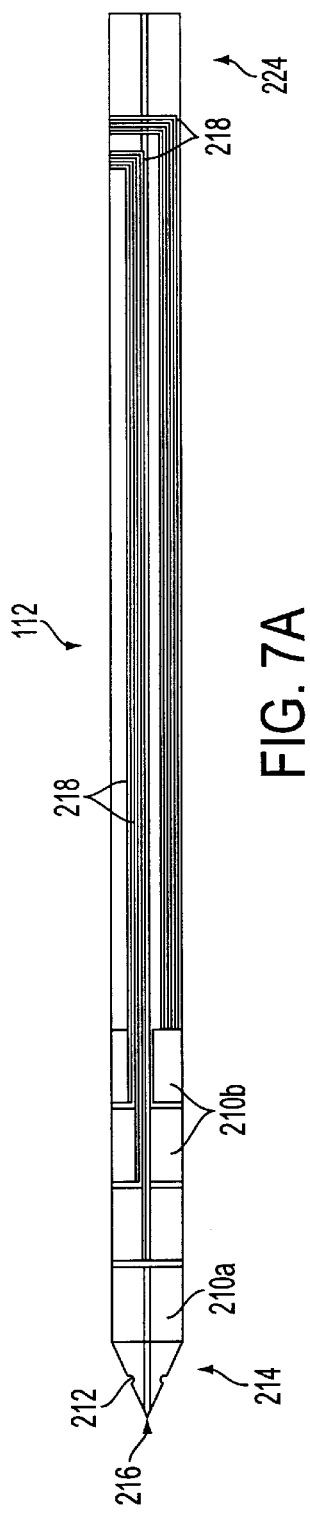
FIG. 7A shows a side view of a needle including the sensors and conducting lines.

In one embodiment treatments of the affected tissue are performed, controlled and varied in three dimensions as well as two dimensions through generators or sensors 210 formed on the needle 112. The needles 112 are inserted through the template 110 and into the affected tissue to be treated. FIG. 7A depicts one embodiment of a multipurpose needle 112 of the present invention that can be used in cooperation with the template 110. The needle 112 can be constructed of any metal or polymer biocompatible material. Examples include stainless steel, Teflon, and polyimide tubing. Generally, the needle 112 is designed to be hollow which allows for a plurality of treatments to be performed. For example, the delivery of treatment or therapeutical substances, including chemicals, drugs, gene therapy vectors and other therapeutic agents, into the tissue to be treated through injection apertures 212 which are located at a first end 214 of the needle 112. Alternatively, a hollow needle 112 can be used for the taking of a biopsy or tissue samples. The needle 112 can also be used to deliver radioactive pellets into the affected tissue. The needle 112 can also be solid for other uses. The first end 214 of the needle 112 can also have a point 216 to ease insertion into the tissue to be treated. Also located near the first end 214 are a plurality of generators or sensors 210 which can be formed on the needle 112 to perform a variety of functions or treatments. The sensors will be discussed in more detail below. Each sensor 210 formed on the needle 112 is also coupled to a conducting strip 218. The conductive strip 218 provides electrical coupling between the sensors 210 and the template 110. Each conducting strip 218 is coupled to a sensor 210 and runs the longitudinal axis 222 of the needle 112 from the sensors 210 at the first end 214 of the needle 112 to approximately the second end 224 of the needle 112. The conducting strips 218 contact and electrically couple to the electrical contact device 170 which allows the conducting strips 218 to transmit signals from the processor 124 through the conductive apertures 142 to the sensors 210 and to transmit signals from the sensors 210 to the processor 124 through the conductive apertures 142 of the PCB 118.

FIG. 8A shows one embodiment of a needle 112 which is constructed with at least one groove 226 which spirals or corkscrews along the longitudinal axis of the needle 112 and optical pattern 230. This spiral groove 226 promotes the rotation of the needle 112 as it is inserted into the tissue to be treated. The rotation of the needle 112 allows for straighter insertion of the needle 112 into the tissue to be treated for more accurate placement of the sensors 210. The spiral groove 226 can also engage pins 228 positioned on the interior of the apertures 116 of the rigid plate 114, as shown in FIG. 8B. The pins further promote the rotation of the needle 112 as it is inserted. Optical pattern 230 allows for precise determination of the insertion depth of needle 112 into the patient to further ensure accurate placement of sensors 210 within the affected tissue.

The formation of a plurality of sensors 210 onto a single needle 112 provides significant advantages over the prior art. By including a plurality of sensors 210 to be formed on a single needle 112, a plurality of treatments can be performed simultaneously in three dimensions without the need to remove one needle and replace it with another needle to perform a different treatment or function. The processor 124 can signal to a first sensor or group of sensors to perform a treatment while the processor signals a second sensor or group of sensors to sense the progress of the treatment and signal the progress back to the processor 124. The processor 124 can then analyze the progress and adjust the treatment according to the treatment plan through the first sensor or group of sensors. The differing types of generators or sensors 210 are well know in the art and can include the ability to measure temperature, to generate heat, to generate an electrical signal which propagates through the tissue being treated, to sense the presence or absence of a specific chemical, to measure radiation, to generate ultrasound wavelengths to be propagated through the tissue to be treated, along with others. The sensors 210 can be formed on the needle 112 through known lithography techniques or other techniques known in the art. Thermocouples can be formed from thermocouple junction materials, such as copper and constantan, and packaged in an insulating sleeve. Resistive temperature detectors (RTD) are formed from, for example, platinum. Ultrasound generators are formed of a series of piezoelectric elements.

Referring back to FIG. 7A, the plurality of sensors 210 can be dispersed over the outer surface of the needle 112 in any predetermined pattern desired, including circumferentially and along the longitudinal axis. In one embodiment sensor 210a is formed in bands, which can completely surround the circumference of the needle 112. Sensor 210b is segmented and only covers a portion of the circumference of the needle 112. The pattern of the sensors 210 can also extend from the first end 214 of the needle towards the second end 224. By providing a plurality of sensors 210 on a single needle 112 dispersed not only circumferentially, but also longitudinally, the treatment of the affected tissue can be implemented, monitored and controlled in a three dimensional approach. Further, by including different sensors 210 with differing characteristics on a single needle 112, a single needle 112 can perform multiple treatments and can also monitor those treatments. Further, by utilizing the template 110 to provide a plurality of needles within the tissue to be treated, neighboring needles 112 can also perform treatments and act as monitors in three dimensions for treatments and functions being performed by other needles 112. Neighboring needles 112 can also act as cooperating treatment sensors to provide cooperation between needles, for example in applying voltage differences for electroporation, also performed and controlled in three dimensions.

The monitoring sensors 210, such as the sensor to measure temperature, sense the presence of a chemical, monitor radiation, etc., transmit information through the conducting strips 218 of the needle 112, through the electrical contact device 170 to the conductive aperture, through the conductive leads 154 to the processor 124. The processor 124 can then evaluate the information provided by the monitoring sensors 210 to adjust the treatment according to the predetermined treatment plan that is stored in the memory of the processor 124. The processor 124 can then adjust the treatment based on the information received from the monitoring sensors 210 by sending control signals to the treatment sensors 210, e.g., RF delivery of heat, electrical signal or waveform generators and such. Because the needles 112 include a plurality of sensors 210 dispersed circumferentially and along the longitudinal axis, the treatments can be monitored and varied in three dimensions, and thus implicitly in two dimensions, providing for higher precision, greater flexibility and more accurate treatment of the affected tissue.

Figure 7B:
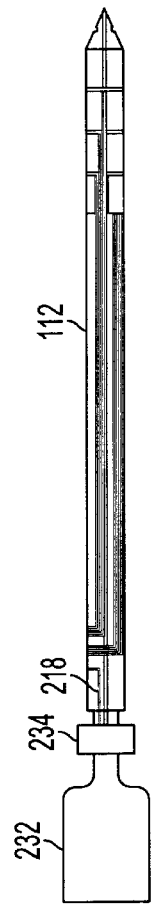
FIG. 7B shows a side view of a needle coupled to a reservoir for the delivery of therapeutical substances into a patient.
Figure 7C:
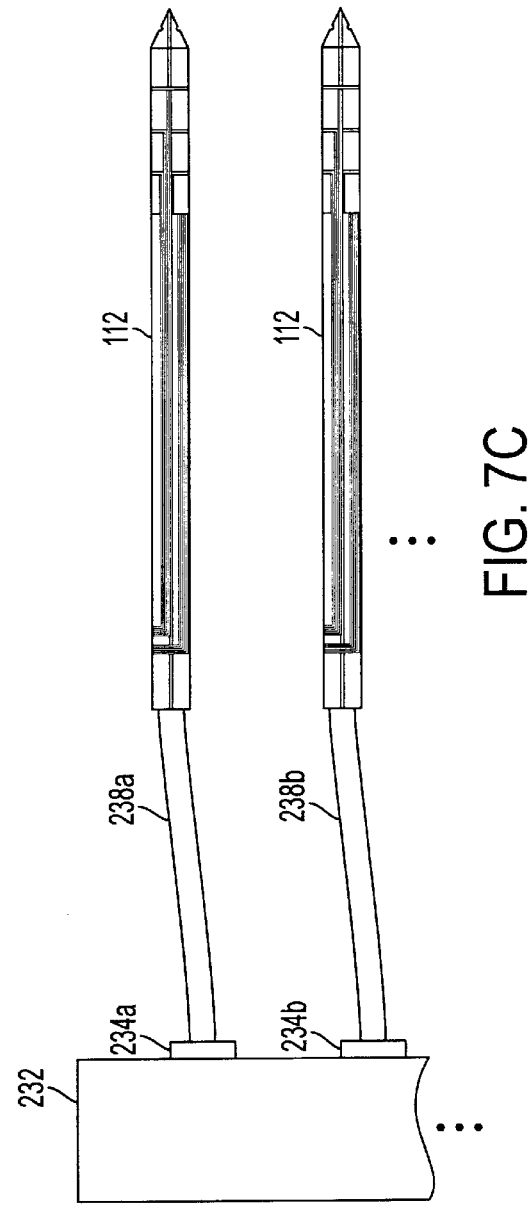
FIG. 7C shows a side view of two needles coupled to a reservoir through tubes for the deliver of therapeutical substances into a patient.

FIG. 7B shows a needle which includes a reservoir for holding various therapy solutions, for example agents and gene therapies, which can be delivered into the affected tissue by a plunger or pump 234 which is also positioned on the needle 112. The plunger 234 can be electrically coupled to a conducting strip 218 on the needle which is coupled to the processor 124 through the template 110. Or alternatively, the plunger switch can be directly coupled to the processor. The processor 110 can direct the plunger, according to the treatment plan, to initiate or stop the plunging of the therapy solution within the cylinder so as to deliver a defined amount of therapy solution into the affected tissue. Alternatively, FIG. 7C shows a reservoir 232 which can be coupled to a plurality of tubes 238a–b coupled to a plurality of needles 112 to allow the injection of therapy solutions. Each needle being coupled to an individual plunger or pump 234a–b for delivering the therapy solutions.

FIG. 7D shows the first end of three needles 112a–c operating simultaneously, each including a plurality of sensors 210 on each needle 112a–c. The plurality of sensors 210 allow the present invention to implement, monitor, control and vary a treatment plan in three dimensions. For example, sensors 210a, b, e, and h of needle 112a and sensor 210j of needle 112b can be temperature sensors. Each can measure the temperature of the surrounding tissue and forward that temperature to the processor 124 (not shown). Sensors 210c, d and f can be heat generating sensors. If 210b reports a temperature at or above a given threshold, the processor 124 can signal sensor 210d to stop producing heat, while allowing 210c, f and sensors of other needles to continue to generate heat. In a further example, sensors 210i and l of needle 112b can be chemical sensors which register the presence of a certain chemical. Sensors 210k and 210m can be designed to generate an electrical pulse signal for electroporation which can be received by sensors 210o and 210r of needle 112c. While the chemical is present within the given tissue being treated, sensors 210k and 210m will generate electric pulses causing cell membranes of the affected tissue to allow the chemical to pass into the cells. If sensor 210i no longer senses the presence of the chemical, the processor can halt the electric pulse signals from sensor 210k while allowing the pulse signal to continue from 210m. This demonstrates the three dimensional effects that the multipurpose template 110 and multipurpose needles 112 with a plurality of sensors 210 spaced both circumferentially and longitudinally provide.

Figure 9:
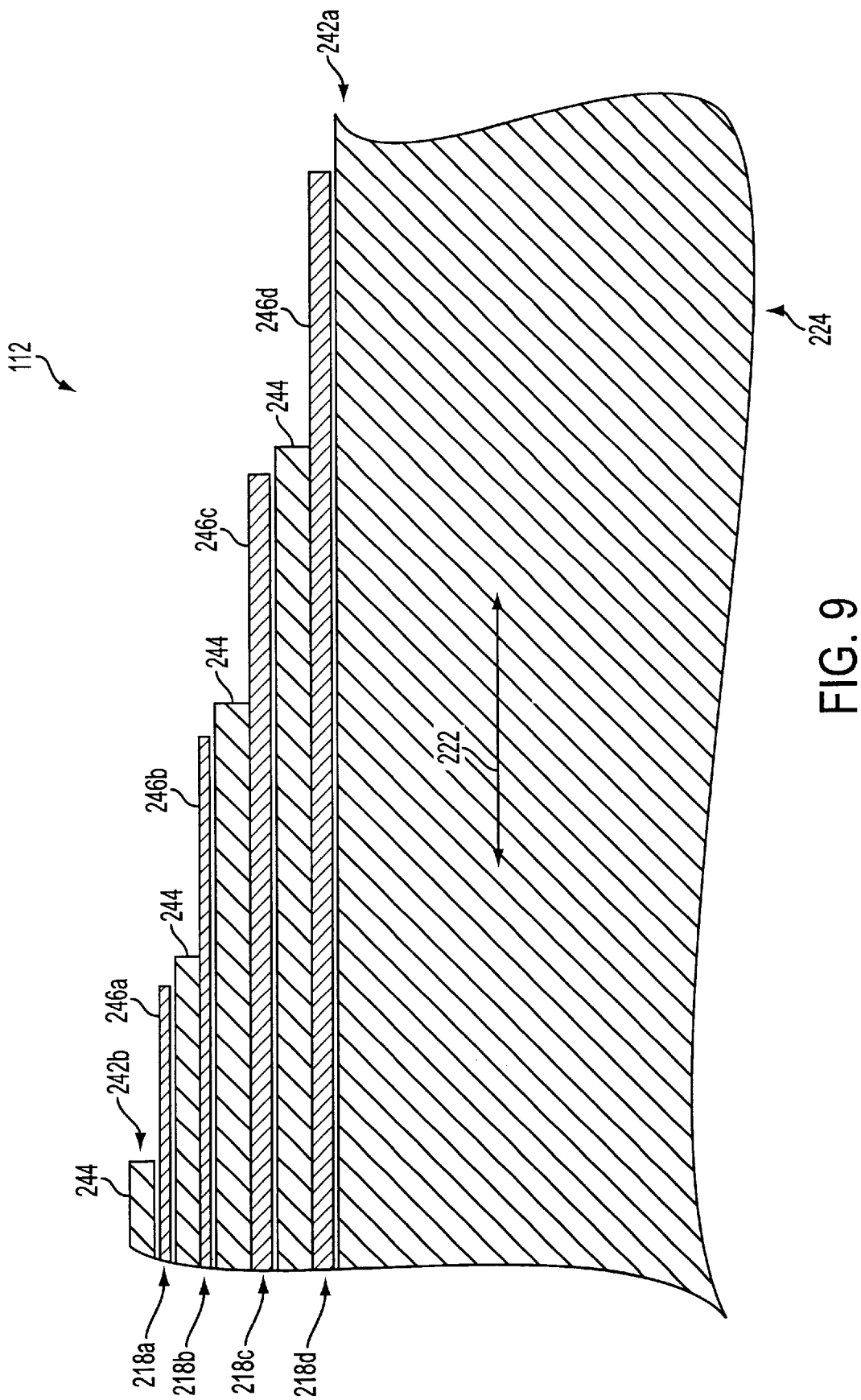
FIG. 9 shows an enlarged partial sectional view of a second end of a needle depicting the conducting strips.

Referring back FIG. 7A, the conducting strips 218 which run longitudinally along the length of the needle 112 can be formed using similar methods as are used to form the sensors 210. Lithography techniques can be used to etch the strips 218, for example, parallel to one another on an outer surface of the needle 112 along the longitudinal axis 222. Individual exposed locations 246 can be formed in a staggered pattern (not shown) to allow coupling to the electrical contact device 170. Alternatively, the conducting strips 218 can be formed stacked one on top of the other, as shown in FIG. 9, showing a cross-sectional view near the second end 224 of a needle 112. In one embodiment the exposed locations 246 are dispersed circumferentially around the needle 112 such that a single conducting strip contacts the conductive section 178 formed on the electrical contact device 170. The conducting strips 218a–d can be formed from an inner diameter 242a to an outer diameter 242b with insulation 244 between the conducting strips 218a–d. The conducting strips 218a–d are progressively exposed at locations 246a–d along the longitudinal axis 222 to allow individual contact with the electrical contact device 170 (not shown). The conducting strips 218 can also be formed from a plurality of concentric metal cylinders separated by insulation 244. Other methods for forming the conducting strips 218 include: forming ridged needles which shadows the metallization into patterns; laser etching; or mechanically scribing the needle surface metal into patterns. The conducting strips 218 can be made of any conductive material that has low enough resistivity and the proper biocompatibility for the application intended.

Conductive strips 218 contact and thus are electrically coupled to the electrical contact device 170. The conducting strips 218 are electrically insulated from each other and from the outside. In one embodiment each conducting strip 218 is exposed in one location 246 near the second end 224. Conducting strips 218 makes contact at the exposed location 246 with one electrical contact device 170. The exposed locations 246 are placed sequentially along the longitudinal axis 222 of the needle 112 so that each electrical contact device 170 is electrically connected to one conducting strip 218. There is a separate electrical contact device 170 for each conducting strip 218. Each electrical contact device 170 connects to one conductive aperture 142 on one PCB 118.

Figure 10A:
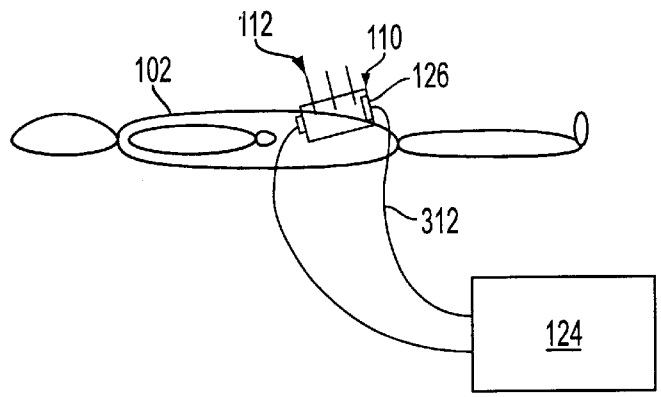
FIG. 10A shows a schematic view of the template, needles and processor in use on a patient.

FIG. 10A depicts the implementation of the multipurpose template 110 together with needles 112 and processor 124. The processor 124 is used to implement and control the treatment plan. The template 110 is fixed to a patient 102 through suturing or other means as is known in the art. Then the needles 112 can be inserted into the apertures 116 of the template 110. The connector ports 156 are coupled to the processor lines 312 which directly connect with the processor 124. The processor 124 implements and controls the treatment according to the treatment plan. Further, the processor 124 can be used to verify the type of needle 112 and the types of sensors 210 on the needle 112.

Figure 10B:
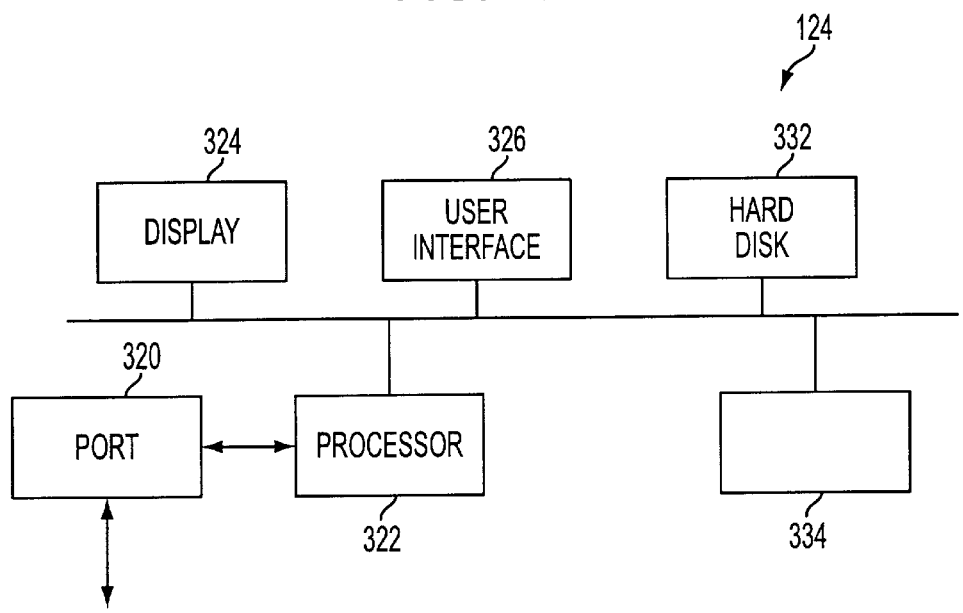
FIG. 10B shows an expanded block diagram of the processor of FIG. 10A.

One embodiment of a processor which is implemented in the present invention is shown in FIG. 10B. The processor 124 includes a port 320 which couples to the processor line 312 or other processor units (not shown) for transmitting and receiving signals to and from the template 110. The port 320 is coupled to an internal processor 322 which controls the processing of the transmitted and received signals. The internal processor 322 is coupled to a display 324, a user interface 326 and memory 332. The display 324 can be a computer monitor, scope monitor, digital display or other well know displays. The user interface can be a keyboard, a mouse, a touch pad, touch screen, control knobs or other well know user interfaces. The memory 332 includes a primary memory 334, which stores the treatment plan and other programs to perform the monitoring and generation of treatment signals to be forwarded to the appropriate needles 112, through the internal processor 322.

The processor 124 is programmed to receive the treatment plan and a program to implement and control the treatment plan based on feedback received from the sensors 210. Alternatively, the processor 124 can be a temperature monitoring device directly connected to a flexible PCB 118 to monitor the temperature of the tissue being treated in three dimensions, or a signal generator, such as an RF generator for heating or a high voltage alternating source which can be used to generate electrical signals during electroporation therapy, or a radiation source. The processor 124 can also be a combination of elements coupled together, each receiving and sending signals to sensors 210 on the needles 112, and controlled by a central processor 124 or computer.

Figure 11:
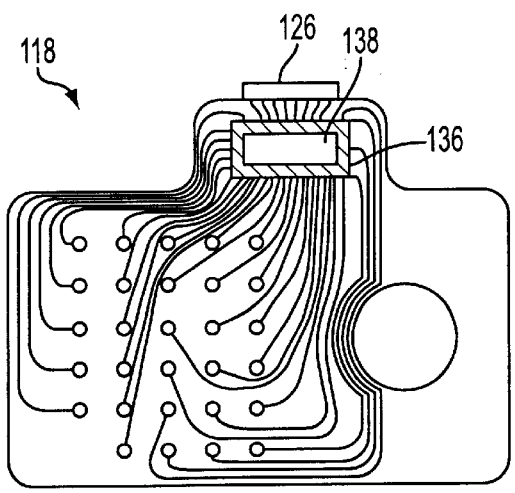
FIG. 11 shows a top view of a flexible PCB including a microprocessor connector and microprocessor.

The processor 124 can also be a microprocessor 138 directly connected on the flexible PCB 118 as depicted in FIG. 11. The microprocessor 138 is programmable through a connector port 126 to receive a treatment plan and to implement and control treatment according to the treatment plan. The microprocessor 138 controls the flexible PCB 118 to which it is connected. Alternatively, the microprocessor 138 is fixed to the rigid plate 114 and coupled to the connector ports 126 of multiple flexible PCBs 118. Further, the microprocessor 138 can be coupled directly to a flexible PCB 118 and configured to control multiple PCBs 118 through the connector port 126.

Figure 12:
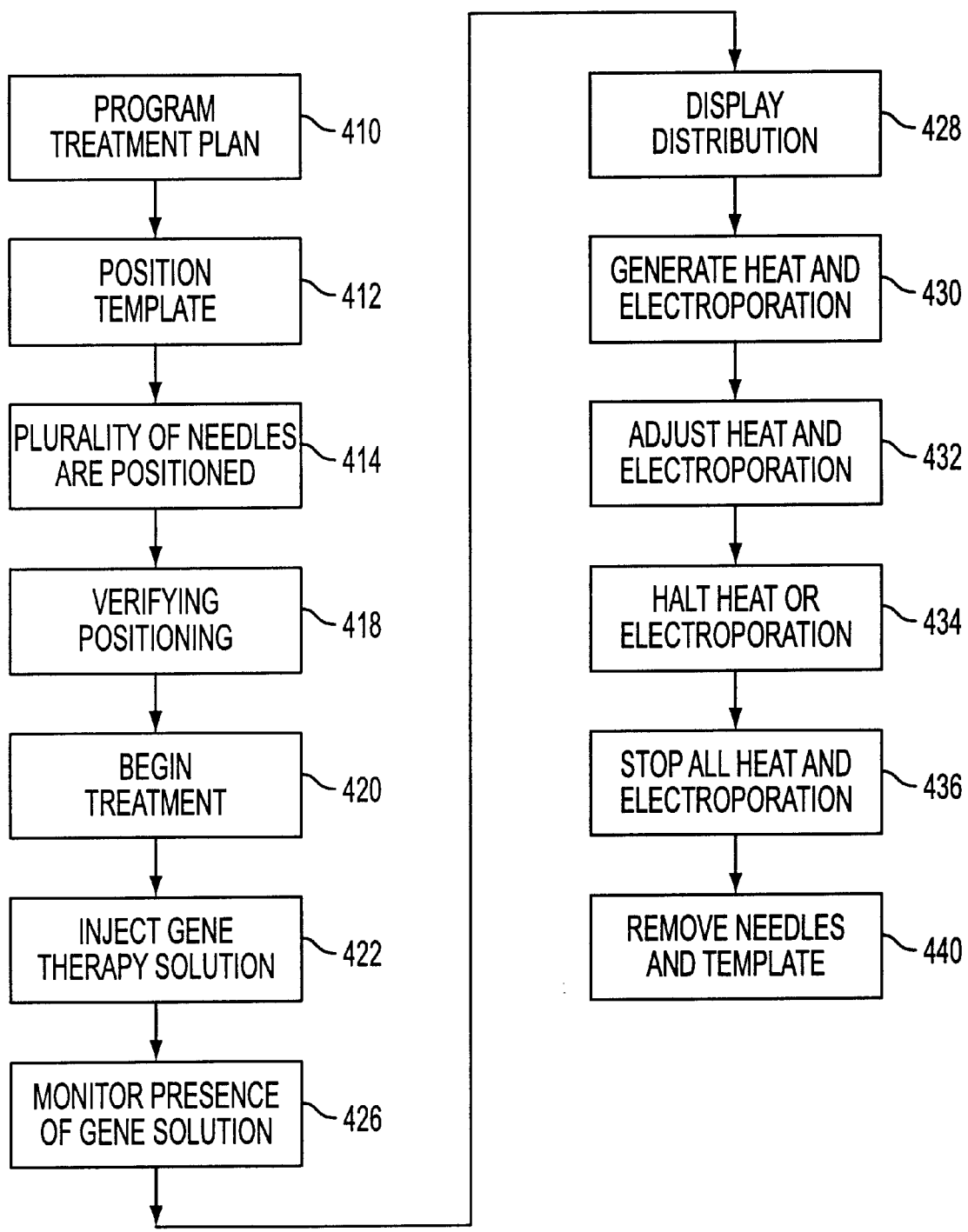
FIG. 12 is a flow diagram of the steps performed in the implementation of the present invention.

One example of the implementation of the multipurpose template 110 in combination with the multipurpose needles 112 is shown in FIG. 12. A patient 102 is diagnosed with a tumor or cancerous growth 104 within the body which requires therapeutic treatment, for example gene therapy with the aid of electroporation and ultrasound. The physician determines the location of the affected tissue 104 and determines the necessary treatment plan. In a first step 410, the processor 124 is programed with the treatment plan. In the second step 412, the template 110 is positioned on the patient 102 according to the physicians determination of the location of the affected tissue 104 and fixed to the patient by suturing. In a third step 414, a plurality of needles 112 according to the treatment plan are inserted into the body of the patient 102 through the template 110 which guides the needles for accurate and stable positioning of the needles 112. In a fourth step 418, the processor 124 instructs at least one of the needles 112 inserted into the patient 102 to produce ultrasound waves through piezoelectric diodes formed within the needle 112. An ultrasound receiver is positioned into the template 110 within the aperture 128. The ultrasound receiver picks up the ultrasound waves generated by the needle 112 and provides the technician or physician with a graphic representation of the positioning of the needles 112 thus verifying the accurate positioning of the needles 112.

In the fifth step 420, once the needles 112 are positioned and verified, the processor 124 starts the treatment plan. In the sixth step 422, a gene therapy solution is injected into the affected tissue 104 through the injection apertures 212 at the first end 214 of a group of needles 112. Sensors 210 on needles 212 are instructed by the processor to monitor the presence of the gene therapy fluid in the seventh step 426. The distribution of the therapy fluid is displayed by the processor 124 on the display 324 in the eighth step 428. In step nine 430, the processor determines which sensors 210 of which needles 212 need to generate heat and which needles 212 need to produce electrical signals for electroporation. The sensors 210 on the plurality of needles 112 continue to signal to the processor 124 the distribution of the gene therapy fluid. As the presence of the gene therapy fluid reaches certain areas, the gene therapy sensors 212 signal the processor. In step ten 432, the processor can adjust the heat generation and electroporation of needles 212 in that area while continuing the heat generation and electroporation in other areas until signaled by the sensors on needles 212 in those other areas trigger the processor 124 to halt heat generation or electroporation in the eleventh step 434. Once the gene therapy fluid is fully dispersed and absorbed according to the treatment plan the heat generation and electroporation is stopped in all needles 112 in the twelfth step 436. In the thirteenth step 440, all of the needles 112 and the template 110 can be removed from the patient 102.

The foregoing descriptions of specific embodiments of the present invention are presented for purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. An apparatus for three dimensionally treating affected tissue within a patient's body according to a treatment plan, comprising:

a template including at least one flexible printed circuit board having a plurality of conductive apertures;

at least one needle having at least one sensor, the needle adapted to insert into and pass through and electrically couple to the conductive apertures;

each conductive aperture is electrically coupled to a conductive lead which electrically couples to at least one connector port; and a processor electrically coupled to at least one of the connector ports and configured to control the sensors of the needle through the template.

2. The apparatus for three dimensionally treating affected tissue within a patient's body as claimed in claim 1, wherein:

the template includes at least one electrical contact device which provides electrical coupling between the needle and the conductive aperture.

3. The apparatus for three dimensionally treating affected tissue within a patient's body as claimed in claim 2, wherein:

the electrical contact device is a compressible foam.

4. The apparatus for three dimensionally treating affected tissue within a patient's body as claimed in claim 1, wherein:

the sensors are formed proximate a first end of the needle;

each sensor is coupled to a conductive strip which extends longitudinally along the needle terminating proximate a second end of the needle such that at least one conductive strip is electrically coupled with the template.

5. The apparatus for three dimensionally treating affected tissue within a patient's body as claimed in claim 4, wherein:

the template includes at least one electrical contact device which provides electrical coupling between the needle and the conductive aperture.

6. The apparatus for three dimensionally treating affected tissue within a patient's body as claimed in claim 1, wherein:

the processor controls the sensors on the needle, such that the processor implements, monitors and adjusts the implementation of the treatment plan in three dimensions.

7. An apparatus for delivering and monitoring a plurality of minimally invasive therapies in the treatment of a medical condition of a patient, the treatment being based on a treatment plan, the apparatus comprising:

a template having a plurality of electrically conductive apertures;

a plurality of needles, each needle having a plurality of sensors;

at least one of the plurality of needles is inserted through and in electrical contact with one of the conductive apertures;

a processor including memory for storing the treatment plan;

the processor is electrically coupled to the template and is configured to send signals to and receive signals from at least one of the sensors of at least one of the needles inserted through one of the conductive aperture of the template; and the processor further configured to process the signals received from the sensor in relation to the treatment plan and to adjust the signals sent to the sensor to control the treatment.

8. The apparatus for delivering and monitoring a plurality of minimally invasive therapies as claimed in claim 7, wherein:

the template further includes at least one substantially rigid plate having a plurality of apertures; and at least one flexible printed circuit board electrically coupled to the processor including the plurality of electrically conductive apertures and a conductive lead extending from each of the conductive apertures and terminating in at least one connector port, the printed circuit board being removably fixed to the rigid plate and positioned such that at least one of the plurality of conductive apertures aligns with one of the apertures of the rigid plate.

9. The apparatus for delivering and monitoring a plurality of minimally invasive therapies as claimed in claim 8, wherein:

a first group of the conductive leads extending from a first group of the conductive apertures of the printed circuit board extend to a first connector port;

a second group of the conductive leads extending from a second group of the conductive apertures of the printed circuit board extend to a second connector port.

10. The apparatus for delivering and monitoring a plurality of minimally invasive therapies as claimed in claim 8, wherein:

the rigid plate includes at least one pin extending from and into the aperture such that the pin engages a groove on the needle to align the needle.

11. The apparatus for delivering and monitoring a plurality of minimally invasive therapies as claimed in claim 7, further comprising:

at least one micromotor coupled to the template adjacent at least one of the conductive apertures of the template configured to receive the needle to be inserted into the conductive aperture and to advance the needle into or retract the needle out of the conductive aperture; and the micromotor is electrically coupled to the processor wherein the processor controls the direction and duration of operation of the motor.

12. The apparatus for delivering and monitoring a plurality of minimally invasive therapies, as claimed in claim 7, wherein:

the template further includes at least one substantially rigid plate having a plurality of apertures;

a plurality of printed circuit boards removably fixed to the rigid plate;

each circuit board having the plurality of conductive apertures wherein the plurality of conductive apertures of the printed circuit boards alien with the plurality of apertures of the rigid plate; and each printed circuit board of the plurality of printed circuit boards are electrically separated.

13. The apparatus for delivering and monitoring a plurality of minimally invasive therapies as claimed in claim 12, wherein:

the processor directs each printed circuit board of the plurality of printed circuit boards to provide different signals to or receive different signals from the needles inserted through the conductive apertures.

14. The apparatus for delivering and monitoring a plurality of minimally invasive therapies as claimed in claim 7, wherein:

the template includes an electrical contact device such that the electrical contact between the needle and the conductive aperture is achieved through the electrical contact device positioned in electrical contact with the conductive aperture; and the needle is inserted through the conductive aperture of the template proximate the electrical contact device and in electrical contact with the electrical contact device.

15. The apparatus for delivering and monitoring a plurality of minimally invasive therapies as claimed in claim 14, wherein:
the electrical contact device is compressible such that the needle is in compressed electrical contact with the electrical contact device when the needle is inserted through the conductive aperture.

16. The apparatus for delivering and monitoring a plurality of minimally invasive therapies as claimed in claim 14, wherein:
the electrical contact device is made of an electrically conductive foam.

17. The apparatus for delivering and monitoring a plurality of minimally invasive therapies as claimed in claim 7, wherein:
the processor including a computer.

18. The apparatus for delivering and monitoring a plurality of minimally invasive therapies as claimed in claim 7, wherein:
the processor including a monitoring device.

19. The apparatus for delivering and monitoring a plurality of minimally invasive therapies as claimed in claim 7, wherein:
the processor including a signal generator.

20. The apparatus for delivering and monitoring a plurality of minimally invasive therapies as claimed in claim 7, wherein:
the processor is a microprocessor fixed on the flexible printed circuit board.

21. The apparatus for delivering and monitoring a plurality of minimally invasive therapies as claimed in claim 7, wherein:
the processor is programmable to receive a program to implement the treatment plan and to cause the treatment plan to be implemented.

22. The apparatus for delivering and monitoring a plurality of minimally invasive therapies as claimed in claim 7, wherein:
the needle having at least one aperture proximate a first end to allow the delivery of a therapeutical substance into the patient.

23. The apparatus for delivering and monitoring a plurality of minimally invasive therapies as claimed in claim 7, wherein:
the needle is configured to generate ultrasonic signals.

24. The apparatus for delivering and monitoring a plurality of minimally invasive therapies as claimed in claim 7, wherein:
the needle includes a plurality of sensors proximate a first end and distributed both circumferentially and along the longitudinal axis.

25. The apparatus for delivering and monitoring a plurality of minimally invasive therapies as claimed in claim 7, wherein:
the needle includes at least one spiral groove on the exterior of the needle extending from approximately a first end to approximately a second end to promote rotation of the needle.

26. The apparatus for delivering and monitoring a plurality of minimally invasive therapies as claimed in claim 7, wherein:
the needle is coupled to a reservoir for holding a therapeutical substance and a plunger for delivering the therapeutical substance through the needle into affected tissue.

27. The apparatus for delivering and monitoring a plurality of minimally invasive therapies as claimed in claim 7, wherein:
at least one of the sensors of the needle is a temperature sensor for monitoring the temperature of tissue surrounding the needle during the treatment.

28. The apparatus for delivering and monitoring a plurality of minimally invasive therapies as claimed in claim 7, wherein:
at least one of the sensors is a heat generator which generates heat to heat up tissue surrounding the needle during the treatment.

29. The apparatus for delivering and monitoring a plurality of minimally invasive therapies as claimed in claim 7, wherein:
at least one of the sensors is an electrical signal generator which generates electrical signals that propagate through tissue surrounding the needle during the treatment.

30. The apparatus for delivering and monitoring a plurality of minimally invasive therapies as claimed in claim 7, wherein:
at least one of the sensors is a chemical sensor which detects the presence of a chemical in tissue surrounding the needle during the treatment.

31. The apparatus for delivering and monitoring a plurality of minimally invasive therapies as claimed in claim 7, wherein:
each one of the plurality sensors is operated independently.

32. The apparatus for delivering and monitoring a plurality of minimally invasive therapies as claimed in claim 7, wherein:
the needle includes at least one conducting strip electrically coupled to at least one sensor and extending along a longitudinal axis of the needle terminating proximate a second end of the needle; and
the conductive strip is electrically coupled with at least one conductive aperture and configured for receiving signals from the processor and transmitting the signals to the sensor and for transmitting signals from the sensor to the processor.

33. The apparatus for delivering and monitoring a plurality of minimally invasive therapies as claimed in claim 32, wherein:
the needle includes a plurality of conducting strips such that the conducting strips extend along the longitudinal axis and are parallel to each other.

34. The apparatus for delivering and monitoring a plurality of minimally invasive therapies as claimed in claim 32, wherein:
the needle includes a plurality of conducting strips such that the conducting strips extending along the longitudinal axis are positioned one on top of the other from an inner radius to an outer radius and separated by insulation.

35. The apparatus for delivering and monitoring a plurality of minimally invasive therapies as claimed in claim 32, wherein:

the needle includes a pattern dispersed along the longitudinal axis to allow monitoring of insertion depth of the needle.

36. A method of performing a minimally invasive treatment plan on an affected portion of a body of a patient, comprising:

fixing a template to a patient's body proximate the affected portion of the body;

inserting a plurality of needles which include a plurality of sensors into the affected portion of the body through the template;

implementing a treatment plan;

monitoring the progress of the treatment plan in three dimensions; and adjusting the implementation of the treatment plan in three dimensions.

37. The method of performing a minimally invasive treatment plan as claimed in claim 36, wherein:

controlling the implementing, monitoring and adjusting of the treatment plan through a processor.

38. The method of performing a minimally invasive treatment plan as claimed in claim 37, wherein:

monitoring the progress of the treatment plan through signals sent from at least one of the sensor on at least one of the needles to the processor.

39. The method of performing a minimally invasive treatment plan as claimed in claim 37, wherein:

adjusting the implementation of the treatment plan by controlling at least one of the sensor on at least one of the needles.

40. The method of performing a minimally invasive treatment plan as claimed in claim 36, further comprising:

verifying through the processor the positioning of the needles within the affected portion of the body prior to implementing the treatment plan.

41. The method of performing a minimally invasive treatment plan as claimed in claim 40, wherein:

verifying the positioning including:

generating ultrasound waves from at least one of the needles within the affected portion of the body; and receiving and displaying an image produced by the ultrasound waves.

42. The method of performing a minimally invasive treatment plan as claimed in claim 36, further comprising:

verifying the needle type inserted into the patient prior to implementing the treatment plan.

43. An apparatus for implementing and monitoring a treatment plan for the treatment of an affected portion of a patient's body, comprising:

a means for positioning a plurality of needles into an affected portion of a patient's body;

the needles include a means for three dimensionally applying and sensing treatments of a treatment plan;

the needles are electrically coupled to the means for positioning;

the means for positioning is electrically coupled to a means for implementing and controlling the treatment plan.

44. The apparatus for implementing and monitoring a treatment plan as claimed in claim 43, wherein:

the means for positioning further includes a means for providing electrical coupling between the needle and the means for implementing and controlling the treatment plan.

45. The apparatus for implementing and monitoring a treatment plan as claimed in claim 44, wherein:

the means for providing electrical coupling between the needle and the means for implementing and controlling includes a plurality of electrically conductive apertures which the needles are inserted through.

46. The apparatus for implementing and monitoring a treatment plan as claimed in claim 45, wherein:

the means for positioning further includes a means for electrically coupling the needle to the electrically conductive aperture.

47. The apparatus for implementing and monitoring a treatment plan as claimed in claim 43, wherein:

the needle includes a means for electrically coupling the means for three dimensionally applying and sensing treatments to the means for positioning.

* * * * *